United States Patent [19]

Chiang et al.

[11] Patent Number: 5,026,897
[45] Date of Patent: Jun. 25, 1991

[54] CARBAPHENS: APROPHEN ANALOGS THAT ARE BINARY ANTIDOTES FOR ORGANOPHOSPHATE POISONING

[75] Inventors: Peter K. Chiang, Bethesda, Md.; Haim Leader, Ramat Hasharm, Israel; Ruthann M. Smejkal, Silver Spring; Richard K. Gordon, Rockville, both of Md.; Charlotte S. Payne, Washington, D.C.; Bhupendra P. Doctor, Potomac; Felipe N. Padilla, Wheaton, both of Md.

[73] Assignee: The United States of America, as represented by the Secretary of the Army, Washington, D.C.

[21] Appl. No.: 580,223

[22] Filed: Sep. 10, 1990

Related U.S. Application Data

[62] Division of Ser. No. 325,806, Mar. 17, 1989.

[51] Int. Cl.$^5$ .............................................. C07C 69/76
[52] U.S. Cl. ...................................... 560/58; 514/534
[58] Field of Search ........................................... 560/58

[56] References Cited

PUBLICATIONS

Watts, C. et al, Mol. Pharmacol. 31(5) 541–51, 1987.
Dreyer, E. et al. J. Biol. Chem. 261(29) 13727–34 1986.
Banerjee, S. et al. Pharm. Res. 7(7) 746–50 1990.
Triggle, C. Con. J. Physiol. Pharmacol. 57(8) 804–8.

Primary Examiner—Paul J. Killos
Attorney, Agent, or Firm—Werten F. W. Bellamy; Anthony T. Lane

[57] ABSTRACT

Novel carbaphens are provided of the formula

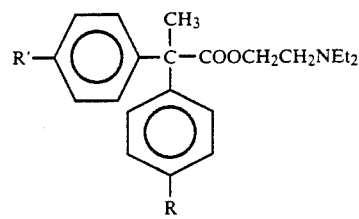

wherein R is OH, $OCON(CH_3)_2$ or $OCONHCH_3$, and R' is H, OH or $_2OCON(CH_3)_2$, stereoisomers thereof, pharmaceutically-acceptable salts thereof or mixtures thereof.

Compositions comprise the carbaphens with pharmaceutically acceptable carriers, and they may further comprise other drugs as well.

Methods of treating patients either prophylactically or therapeutically which suffer from organophosphate poisoning, coronary insufficiency, cerebral vasospasms, spastic cholitis and cholecystitis comprise the administration of the carbaphens of the invention.

14 Claims, No Drawings

CARBAPHENS: APROPHEN ANALOGS THAT ARE BINARY ANTIDOTES FOR ORGANOPHOSPHATE POISONING

This is a division of application Ser. No. 07/325,806, filed Mar. 17, 1989.

TECHNICAL FIELD

This invention relates to carbaphens useful, e.g., against organophosphate poisoning. These compounds are novel aprophen analogs which carry carbamyl substituents on the phenyl rings. These compounds exhibit enhanced therapeutic characteristics of aprophen while being capable of protecting a subject from organophosphate poisoning by chemically masking cholinesterase enzymes.

BACKGROUND ART

Aprophen (N,N-diethylaminoethyl 2,2-diphenylpropionate) is a potent anticholinergic and antispasmodic agent possessing a wide number of distinct pharmacological actions, including both antimuscarinic and noncompetitive nicotinic antagonist activities (Mashkovsky, M. D., Liberman, S. S., Farmakol. Toksikol. (1957), 20: 354; volkova, Z. V., Farmakol. Toksikol. (1959), 22: 348; Witkin, J. M., Gordon, R. K., Chiang, P. K., J. Pharmacol. Exp. Ther. (1987) 242: 796, Carroll, F. I., Abraham, P., Parham, K., Griffith, R. C., Ahmad, A., Richard, M. M., Padilla, F. N., Witkin, J. M., Chiang, P. K., J. Med. Chem. (1987), 30: 805; Brown, N. D., Smejkal, R. M., Breuer, E., Doctor, B. P., Chiang, P. K., J. Pharmaceut. Sci. (1988), 77: 145; Dawson, R. M., Freeman, S. E., and Paddle, B. M., Biochem. Pharmacol. (1985), 34: 1577; Amitai, G., Herz, J. M., Bruckstein, R., and Luz-Chapman, S., Mol. Pharmacol. (1987), 32: 678; Nakazato, Y., Oleshansky, M. A., Chiang, P. K., Arch. Int. Pharmacodyn. (1988), 293: 209; Beach, J. E., Smallridge, R. C., Chiang, P. K., and Fein, H. G., J. Pharmacol. Exp. Ther. (1988), 246: 548).

The potent antimuscarinic and antinicotinic effects of aprophen make it a potential drug of choice in the therapy of poisoning by organophosphate/anticholinesterase agents (Witkin, J. M., and Gordon, R. K., Chiang, P. K., J. Pharmacol. Exp. Ther. (1987), 242, 796; Leadbeater, L., Inns, R. H., Rylands, J. M., Fund. Appl. Toxicol. (1985), 5: S225; Leadbeater, L., D'Mello, G. D., Proc. 2nd Int. Symp. Protection Against Chemical Warfare Agents, Stockholm, Sweden. (1986), pp. 335).

Organophosphates irreversibly inactivate cholinesterases. However, pretreatment with carbamates offers prophylactic protection against organophosphate poisoning because these drugs reversibly carbamylate the active site of cholinesterases. Therefore, the enzymes are chemically sequestered from the action of organophosphates, permitting recovery through decarbamylation (Berry, W. K., Davies, D. R., Biochem. Pharmacol. (1970), 19: 927, Harris, L. W., Heyl, W. C., Stitcher, D. L., Moore, R. D., Life Sci. (1978), 22: 907; Hayashi, E., Okudaira, H., Yamada, S., Tox. Appl. Pharmacol. (1979), 48: 111; Lennox, W. J., Harris, L. W., Talbot, B. G., and Anderson, D. R., Life Sci. (1985), 37: 793; McGee, J., and Brezenoff, H. E., Life Sci. (1987), 41: 65).

The combined administration of aprophen and a carbamate, such as pyridostigmine or physostigmine, significantly improved the protection afforded by either drug against the physiological and behavioral symptoms of organophosphate poisoning, even if post-poisoning treatment were omitted (Amitai, G., Herz, J. M., Bruckstein, R., and Luz-Chapman, S. Mol. Pharmacol. (1987) 32: 678; Nakazato, Y.; Oleshansky, M. A., and Chiang, P. K., Arch. Int. Pharmacodyn. (1988), 293: 209).

DISCLOSURE OF THE INVENTION

This invention relates to a compound of the formula

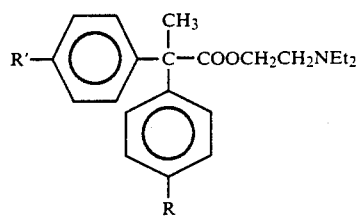

wherein
R is OH, OCON(CH$_3$)$_2$ or OCONHCH$_3$; and
R$^1$ is H, OH or OCON(CH$_3$)$_2$, stereoisomers thereof, pharmaceutically-acceptable salts thereof and mixtures thereof.

This invention also relates to a carbaphen composition, comprising
about 0.001 to 99.999 wt % of a compound of the formula

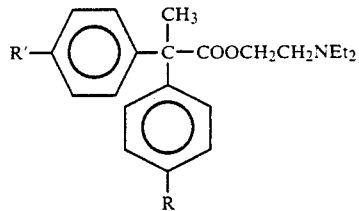

wherein
R is OH, OCON(CH$_3$)$_2$ or OCONHCH$_3$; and
R$^1$ is H, OH or OCON(CH$_3$)$_2$, stereoisomers thereof, pharmaceutically-acceptable salts thereof, and mixtures thereof; and
a pharmaceutically-acceptable carrier.

Also part of this invention is a method of preparing hydroxy aprophen of the formula

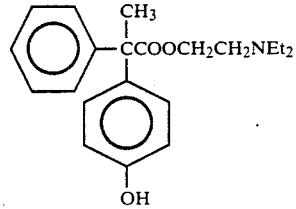

stereoisomers thereof, pharmaceutically-acceptable salts thereof or mixtures thereof comprising (1) reacting 4-halonitrobenzene with alpha-methyl benzyl cyanide in a solvent in the presence of a base to obtain the corresponding para-nitrophenyl substituted nitrile;

(2) hydrolyzing said para-nitrophenyl substituted nitrile in the presence of sulfuric acid under known conditions and then adding an acid halide at reflux to obtain the corresponding propionic acid derivative;

(3) esterifying the propionic acid derivative in the presence of an organic alcohol in an acid medium to obtain the corresponding propionic acid ester;

(4) hydrogenating the NO$_2$-substituent of the phenyl ring of the propionic acid ester to obtain the corresponding amine;

(5) diazotizing the amine under standard conditions and then increasing the temperature to room temperature to obtain a hydroxyphenyl derivative of the propionic acid ester;

(6) hydrolyzing the phenolic derivative of the ester in basic medium under standard conditions to obtain the hydroxyphenyl derivative of the propionic acid; and (7) esterifying the hydroxyphenyl derivative of the propionic acid with a N,N-dialkylaziridinium salt in an aqueous solution to obtain hydroxy aprophen.

A method is also provided for the synthesis of dimethylaminocarbamylaprophen of the formula

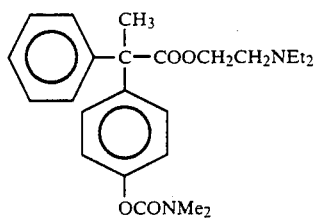

stereoisomers thereof, pharmaceutically-acceptable salts thereof or mixtures thereof, comprising (1) reacting 4-halonitrobenzene with alpha-methyl benzyl cyanide in a solvent in the presence of a base to obtain the corresponding para-nitrophenyl substituted nitrile;

(2) hydrolyzing said para-nitrophenyl substituted nitrile in the presence of sulfuric acid under known conditions and then adding an acid halide at reflux to obtain the corresponding propionic acid derivative;

(3) esterifying the propionic acid derivative in the presence of an organic alcohol in an acid medium to obtain the corresponding propionic acid ester;

(4) hydrogenating the NO$_2$-substituent of the phenyl ring of the propionic acid ester to obtain the corresponding amine;

(5) diazotizing the amine under standard conditions and then increasing the temperature to room temperature to obtain a hydroxyphenyl derivative of the propionic acid ester;

(6) hydrolyzing the phenolic derivative of the ester in basic medium under standard conditions to obtain the hydroxyphenyl derivative of the propionic acid;

(7) esterifying the hydroxyphenyl derivative of the propionic acid with a N,N-dialkylaziridinium salt in an aqueous solution to obtain hydroxy aprophen; and (8) reacting the hydroxy aprophen with excess dimethyl carbamyl halide at high temperature to obtain the dimethylaminocarbamyl aprophen.

A method is also disclosed herein to prepare monomethylcarbamyl aprophen of the formula

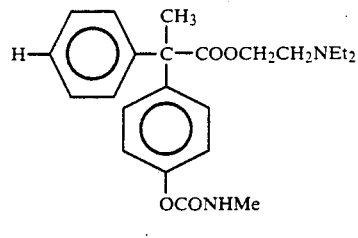

comprising (1) reacting 4-halonitrobenzene with alpha-methyl benzyl cyanide in a solvent in the presence of a base to obtain the corresponding para-nitrophenyl substituted nitrile;

(2) hydrolyzing said para-nitrophenyl substituted nitrile in the presence of sulfuric acid under known conditions and then adding an acid halide at reflux to obtain the corresponding propionic acid derivative;

(3) esterifying the propionic acid derivative in the presence of an organic alcohol in an acid medium to obtain the corresponding propionic acid ester;

(4) hydrogenating the NO$_2$-substituent of the phenyl ring of the propionic acid ester to obtain the corresponding amine;

(5) diazotizing the amine under standard conditions and then increasing the temperature to room temperature to obtain a hydroxyphenyl derivative of the propionic acid ester;

(6) hydrolyzing the phenolic derivative of the ester in basic medium under standard conditions to obtain the hydroxyphenyl derivative of the propionic acid;

(7) esterifying the hydroxyphenyl derivative of the propionic acid with a N,N-dialkylaziridinium salt in an aqueous solution to obtain hydroxy aprophen; and (8) reacting hydroxy aprophen with methylisocyanate in the presence of a catalytic amount of sodium in a solvent to obtain said monomethylcarbamyl aprophen.

Also provided herein is a method for preparing a dihydroxy aprophen of the formula

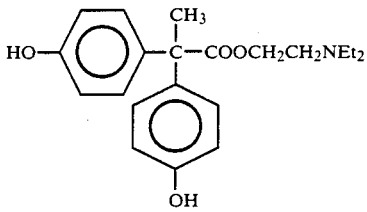

stereoisomers thereof, pharmaceutically-acceptable salts thereof or mixtures thereof comprising (1) reacting phenol with pyruvic acid in an acidic medium to obtain 2,2-bis-(4-hydroxyphenyl) propionic acid; and (2) reacting said 2,2-bis-(4-hydroxyphenyl) propionic acid with an aqueous solution of an N,N-diethylaziridinium salt in a polar solvent to obtain said dihydroxy aprophen.

This invention also relates to a method of preparing a dimethylcarbamate aprophen of the formula

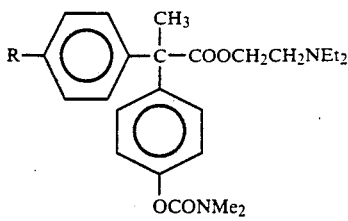

wherein R is OH or OCON(CH$_3$)$_2$, stereoisomers thereof, pharmaceutically-acceptable salts thereof or mixtures thereof, comprising (1) reacting phenol with pyruvic acid in an acidic medium to obtain 2,2-bis-(4-hydroxyphenyl) propionic acid;

(2) reacting said 2,2-bis-(4-hydroxyphenyl) propionic acid with an aqueous solution of an N,N-diethylaziridinium salt in a polar solvent to obtain dihydroxy aprophen; and (3) reacting said dihydroxy aprophen with an equivalent excess of dimethylcarbamyl halide at a temperature of about 70° to 110° C. to obtain said dimethyl carbamate aprophen.

Also part of this invention is a method of inhibiting organophosphate poisoning comprising administering to a subject in need of said inhibition an amount of a compound of the formula

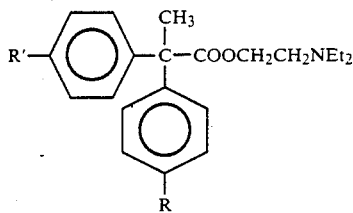

wherein

R is OH, OCON(CH$_3$)$_2$ or OCONHCH$_3$; and

R$^1$ is H, OH or OCON(CH$_3$)$_2$; stereoisomers thereof, pharmaceutically-acceptable salts thereof or mixtures thereof effective to attain said inhibition.

Also part of this invention are the following methods.

A method of treating a subject afflicted with organophosphate poisoning comprising administering to the subject an amount of the compound of the invention effective to attain said effect.

A method of treating a subject afflicted with coronary insufficiency comprising administering to the subject an anti-coronary insufficiency effective amount of the compound of the invention.

A method of treating a subject afflicted with cerebral vasospasms comprising administering to the subject an anti-cerebral vasospasmic effective amount of the compound of this invention.

A method of treating a subject afflicted with spasmic colitis comprising administering to the subject an antispasmic colitic effective amount of the compound of the invention.

A method of treating a subject afflicted with cholecystitis comprising administering to the subject an anticholecystitis effective amount of the compound of the invention.

Other objects, advantages and features of the present invention will become apparent to those skilled in the art from the following discussion.

BEST MODE FOR CARRYING OUT THE INVENTION

This invention arose from a desire to improve on the antidotal efficacy of aprophen, which is an anticholinergic agent, and physostigmine or pyridostygmine, which are carbamates. The inventors reasoned that the carbaphens of the structures described herein would exhibit most of the therapeutic characteristics of aprophen as well as protecting prophylactically by acting as carbamates to chemically mask cholinesterase enzymes. In addition, the inventors expected that the presence of two cholinergic recognition sites per molecule would cause higher local concentrations of the drug to become available at post-synaptic sites.

The carbaphens of the invention are compounds of the formula

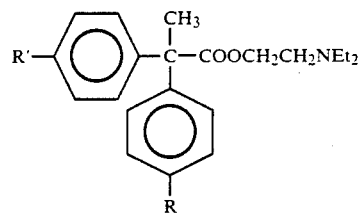

wherein

R is OH, OCON(CH$_3$)$_2$ or OCONHCH$_3$; and

R$^1$ is H, OH or OCON(CH$_3$)$_2$; stereoisomers thereof, pharmaceutically-acceptable salts thereof or mixtures thereof.

The carbaphens of this invention have been found to significantly improve the protection afforded by either drug alone (aprophen or carbamylating agent alone) against the physiological and behavioral symptoms of organophosphate poisoning. The carbaphens of the invention are therefore excellent prophylactic or therapeutic antidotes useful in cases of organophosphate poisoning. They can also be used in combination treatments with other known drugs.

Potential uses for the carbaphen compounds of this invention are the following, among others.

(1) Antidotes for chemcial warfare agents, i.e., organophosphate poisoning.

(2) Antidotes for organophosphate insecticides.

(3) Pharmaceutical drugs for coronary insufficiency.

(4) Pharmaceutical drugs for cerebral vasospasms.

(5) Pharmaceutical drugs for spasmic colitis.

(6) Pharmaceutical drugs for cholecystitis.

The following schemes I and II provide a schematic diagram of the synthesis of the carbaphens of the invention.

Scheme I: Synthetic Pathway of the Substituted Aprophen Derivatives
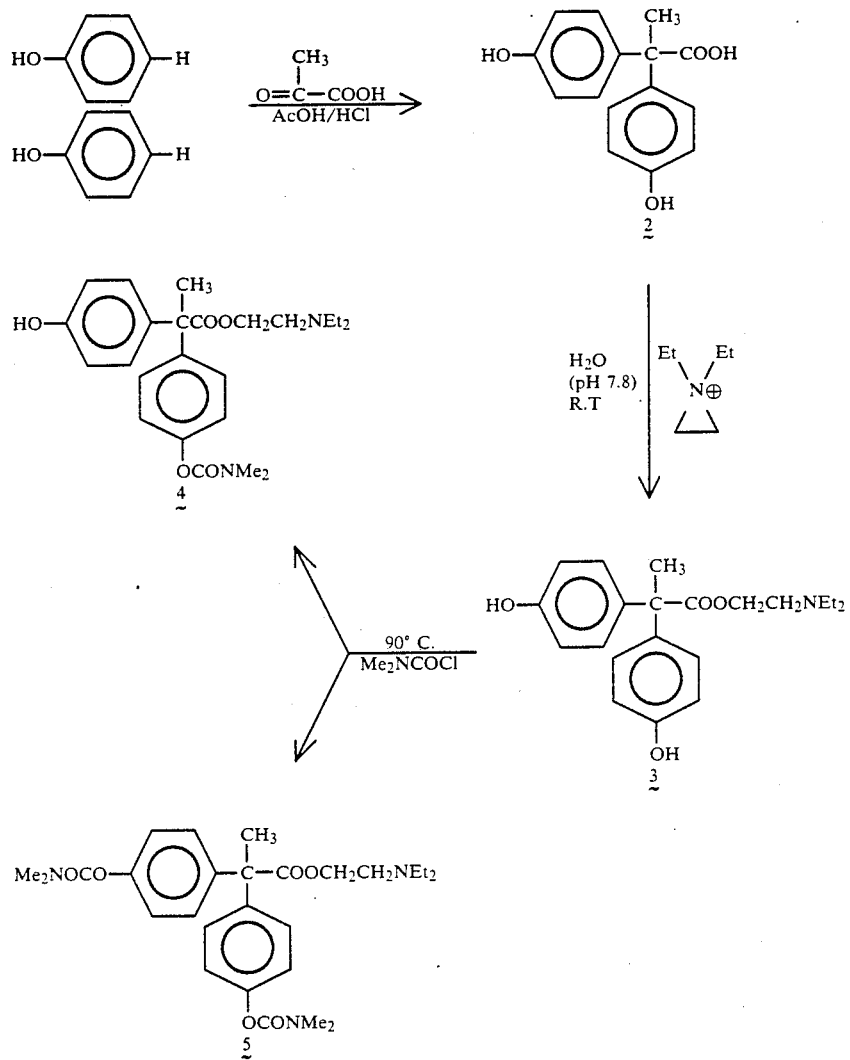
Scheme II: Synthetic Pathway of the Monosubstituted Aprophen Derivatives
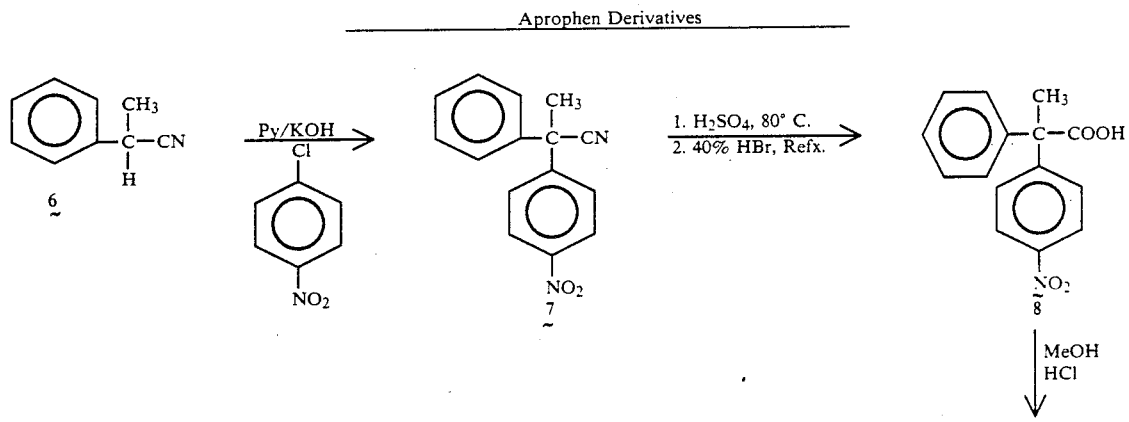

-continued
Scheme II: Synthetic Pathway of the Monosubstituted Aprophen Derivatives

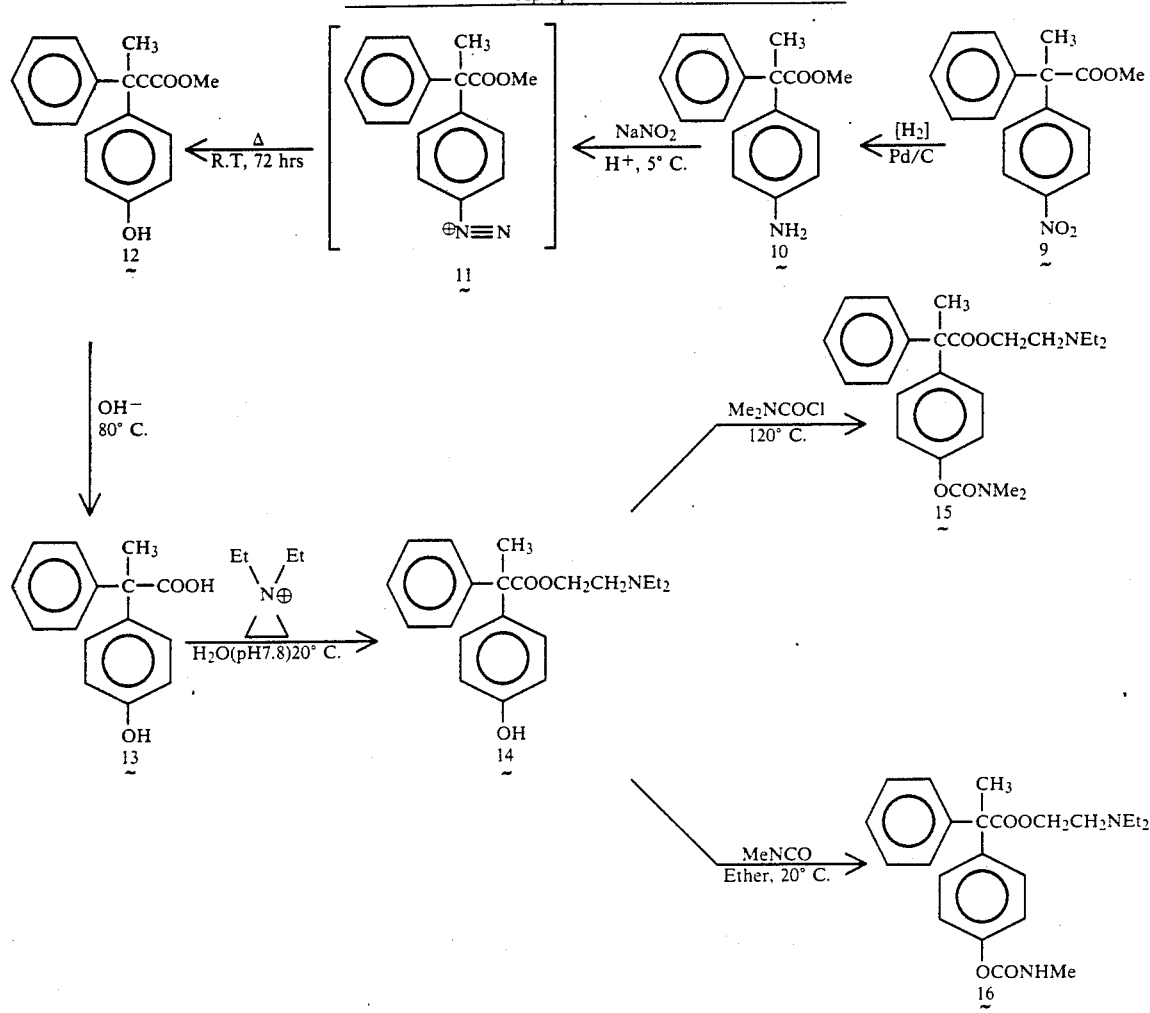

The particular carbaphens which were synthesized by the inventors are shown in Scheme III hereinbelow.

Scheme III: Chemical Structure of the Carbaphens

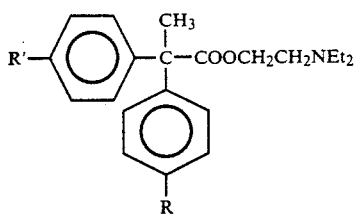

Aprophen R = R' = H
3  R = R' = OH
4  R = OCONMe$_2$, R = OH
5  R = R' = OCONMe$_2$
14 R = OH, R' = H
15 R = OCONMe$_2$, R' = H
16 R = OCOHMe, R' = H stereoisomers thereof, pharmaceutically-acceptable salts thereof and some mixtures thereof.

Some of these compounds are particularly active in a manner similar to physostigmine and pyridostigmine. Examples of these are compounds such as dimethylhydroxy carbaphen (Compound 4), dimethyl carbaphen (Compound 15) and monomethyl carbaphen (Compound 16). These three compounds are found to be highly inhibitory of human butyrylcholinesterase in a time-dependent manner and they also exhibit high potencies on the order of those of physostigmine and pyridostigmine. The latter two compounds (Compounds 15 and 16) exhibit almost the same anti-muscarinic profile as the known compound aprophen. However, these compounds only have a small inhibitory effect of acetylcholinesterase activity. The non-carbamylated analogs have substantially no effect on the activity of either cholinesterase enzyme.

The carbaphen compounds of this invention are therefore prototype drugs which appear to interact with both muscarinic receptors and cholinesterase enzymes. Moreover, these compounds can also be classified as pro-drugs given the fact that after they carbamylate the cholinesterase enzyme they yield hydroxy aprophen (Compound 14) which is itself a potent anti-muscarinic drug.

Particularly important carbaphens of the invention are those wherein

R=R'=OH,

R=R'=OCON(CH$_3$)$_2$,

R is OCON(CH$_3$)$_2$ and R' is H,
R is OCON(CH$_3$)$_2$ and R' is OH,
R is OH and R' is H, and
R is OCONHCH$_3$ and R' is H.

The novel carbaphens of the invention may be formulated in a composition comprising preferably about 0.001 to 99.999 wt % of the compound, the remainder being a filler suitable for the particular use to which the composition is intended. More preferred amounts are about 1 to 90 wt %, and still more preferred about 10 to 80 wt %. In a particularly preferred embodiment of this composition the compound is present in an amount of about 30 to 70 wt %, and even more preferably about 40 to 60 wt %.

Suitable fillers are solid and liquid products. Preferable are pharmaceutically acceptable carriers comprising buffers such as Dulbecco's MEM, Krebs-Ringer medium, phosphate buffered saline and sodium phosphate. These are all known in the art and/or are commercially available. However, other carriers may also be utilized.

The pharmaceutically-acceptable salts of the carbaphens may be prepared by methods known in the art, such as adding an acid to the carbaphen, e.g., in molar equivalent amounts. The types of salts which are pharmaceutically-acceptable are known in the art and need not be further described herein.

The composition of the invention may be prepared by methods known in the art, such as simply mixing, compounding and the like. Particularly preferred forms of compounding the present composition are tablets, capsules, solutions, and the like. However other forms may also be utilized.

Various methods of treating patients are provided in this patent. One of them is a method of prophylactically inhibiting organophosphate poisoning comprising administering to a subject in need of said inhibition an amount of the compound of the invention which is effective to attain the inhibition. Thus, the carbaphens of the invention may be administered as a prophylactive measure prior to organophosphate poisoning or thereafter to treat such condition. Clearly, the compound may be administered by itself or in the form of a composition as described herein. The compound is preferably administered in an amount of about 0.005 to 250 mg or more every about 2 to 24 hours, and more preferably about 0.05 to 50 mg every about 6 to 12 hours, and still more preferably about 0.5 to 25 mg every about 8 to 10 hours. The carbaphen of the invention, either alone or with a carrier, may be administered simultaneously with other drugs, such as antiorganophosphate drugs, known in the art.

Another method provided herein is that of treating a subject afflicted with organophosphate poisoning comprising administering to the subject an amount of the compound of the invention effective to ameliorate said condition. Either by itself or as a composition the carbaphen is administered to e.g., a human, in an amount of about 0.005 to 250 mg or more every about 2 to 24 hours, more preferably about 0.05 to 50 mg every about 6 to 12 hours, and still more preferably about 0.5 to 25 mg every about 10 to 12 hours. Also for this purpose the compound may be administered simultaneously with other anti-organophosphate poisoning drugs.

Also provided herein is a method of treating a subject afflicted with coronary insufficiency comprising administering to said subject an anti-coronary insufficiency effective amount of compound of the invention. As in the previous methods the compound may be administered by itself, or in the form of a composition, which may also comprise another anti-coronary insufficiency drug or simply in joint therapy with such drug. The compound is preferably administered for this particular purpose in an amount of about 0.005 to 250 mg or more every about 2 to 24 hours, more preferably about 0.05 to 50 mg every about 4 to 16 hours, and still more preferably about 0.5 to 25 mg every about 8 to 12 hours.

Also part of the invention is a method of treating a subject afflicted with cerebral vasospasms comprising administering to the subject an anticerebral vasospasmic effective amount of the compound of the invention. The compound may be administered by itself, jointly with other anti-cerebral vasospasmic drugs, or in a composition with a carrier which may also contain other such drugs. In general it may be administered in an amount of about 0.005 to 250 mg or more every about 2 to 24 hours, preferably about 0.05 to 50 mg every about 6 to 18 hours, and more preferably about 0.5 to 25 mg every about 8 to 12 hours.

Another method described herein is that of treating a subject afflicted with spasmic colitis which comprises administering to the subject an anti-spasmic colitic effective amount of the carbaphen of this invention, either by itself, jointly with other anti-colitis drugs or in a composition with a carrier which may additionally contain other anti-spasmic colitis drugs. Typically, the carbaphen of the invention is be administered for this purpose in an amount of about 0.005 to 250 mg or more every about 2 to 24 hours, preferably about 0.05 to 50 mg every about 6 to 18 hours, and more preferably about 0.5 to 25 mg every about 8 to 12 hours.

Also part of this invention is a method of treating a subject afflicted with colicystitis comprising administering to the subject an anti-colicystitic effective amount of the carbaphen of the invention. The carbaphen may be administered by itself, in conjunction with other therapeutic treatments such as other anti-colicystitic drugs or in a composition with a carrier which may further contain other such drugs. Typically, the compound is administered in an amount of about 0.005 to 250 mg or more every about 2 to 24 hours, preferably about 0.05 to 50 mg every about 4 to 18 hours, and more preferably about 0.5 to 25 mg every about 10 to 14 hours.

The synthetic pathway for the mono-carbamyl aprophen derivatives is outlined in Scheme II above. In general, a p-halonitrobenzene is reacted with alpha-methylbenzyl cyanide in a solvent medium leading to a condensation to obtain the p-nitrophenyl substituted nitrile derivative (Compound 7). This compound is hydrolyzed by means of an amide to the corresponding propionic acid derivative (Compound 8). An alkyl ester (Compound 9) of the propionic acid derivative is hydrogenated to the amine (Compound 10) which is then diazotized to an unstable form of a compound (Compound 11) and decomposed at room temperature to obtain the hydroxy alkyl ester derivative (Compound 12).

The conditions for most of these steps are standard and are known in the art. However, the following are applicable to the decomposition of the diazonium salt, the step going from compound 11 to compound 12 in Scheme II. The generation of the parahydroxy compound (12) by heating the acidic diazotization reaction mixture to temperatures as high as about 40° C. fails, resulting in polymeric and other decomposition products. However, the inventors succeeded in obtaining compound (12) under special conditions for the reaction. The reaction mixture must be kept for at least about 72 hours at about 15° to 30° C., and more preferably about room temperature. Secondly, an unidentified by-product is obtained at room temperature (about 25%) which appears to be a coupling product of unreacted diazonium salt (Compound 11) and the hydroxyalkyl ester derivative (Compound 12).

The alkaline hydrolysis of the methyl ester derivative (12) leads to the hydroxy acid (Compound 13) which is then esterified to the hydroxy aprophen derivative (Compound 14) by the addition of N,N-diethylaziridium in an aqueous-bicarbonate solution.

This invention also provides novel methods of preparing the carbaphens of the invention. One such method is that of preparing a hydroxy aprophen of the formula

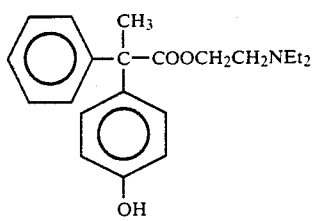

stereoisomers thereof, pharmaceutically-acceptable salts thereof or mixtures thereof, comprising (1) reacting p-halonitrobenzene with alpha-methylbenzyl cyanide in a solvent to obtain a p-NO₂ phenol substituted nitrile of the formula

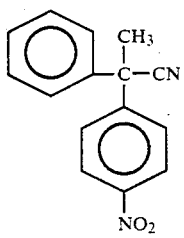

(2) reacting said nitrile first with sulfuric acid and then with HX, where X is Cl, Br or I to obtain the corresponding propionic acid derivative of the formula p

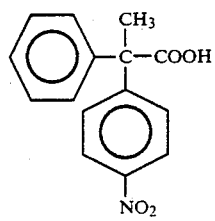

(3) esterifying said propionic acid derivative with a hydroxyalkyl compound to obtain an alkyl ester of the propionic acid;

(4) hydrogenating said ester to obtain an amino derivative of the propionic acid ester of the formula

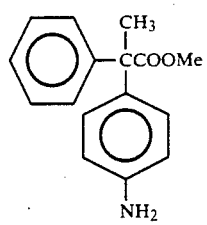

(5) diazotizing said amino derivative and decomposing at room temperature for at least about 72 hours to obtain a hydroxyalkyl ester of the formula

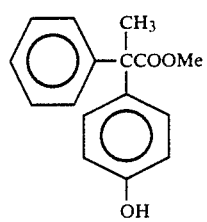

(6) hydrolyzing the hydroxyalkyl ester in an alkaline medium to obtain the corresponding hydroxy propionic acid derivative; and (7) reacting said hydroxy propionic acid derivative with an N,N-diethylaziridium salt in an aqueous solution to obtain said hydroxy aprophen.

A method is also provided herein for preparing a dimethylaminocarbamyl aprophen of the formula

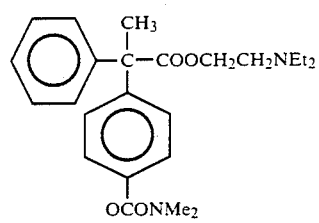

stereoisomers thereof, pharmaceutically-acceptable salts thereof or mixtures thereof, comprising (1) reacting p-halo nitrobenzene with alpha-methyl benzyl cyanide in a solvent to obtain a p-NO₂phenol substituted nitrile of the formula

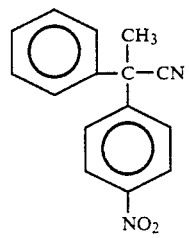

(2) reacting said nitrile first with sulfuric acid and then with HX, where X is Cl, Br or I to obtain the corresponding propionic acid derivative of the formula p

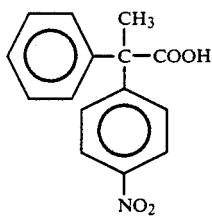 8

(3) esterifying said propionic acid derivative with a hydroxyalkyl compound to obtain an alkyl ester of the propionic acid;

(4) hydrogenating said ester to obtain an amino derivative of the propionic acid ester of the formula

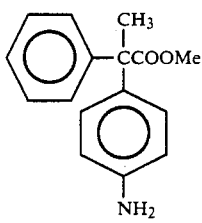 10

(5) diazotizing said amino derivative and decomposing at room temperature for at least about 72 hours to obtain a hydroxyalkyl ester of the formula

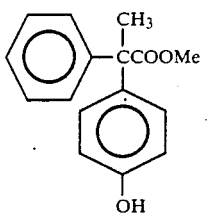 12

(6) hydrolyzing the hydroxyalkyl ester in an alkaline medium to obtain the corresponding hydroxy propionic acid derivative;

(7) reacting said hydroxy propionic acid derivative with an N,N-diethylaziridium salt in an aqueous solution to obtain hydroxy aprophen; and (8) reacting said hydroxy aprophen with an equivalent excess of dimethylcarbamyl halide at a temperature of about 80° to 140° C. to obtain said dimethylaminocarbamyl aprophen.

Steps (1) through (7) of the above method are equivalent to steps (1) to (7) of the previous method. Finally, the hydroxy aprophen is reacted with an equivalent excess of dimethylcarbamyl halide at a temperature of about 80° to 140° C. to obtain the dimethylaminocarbamyl aprophen (Compound 15). This reaction is typically conducted for about thirty minutes to four hours and the product is obtained with a good yield, typically in excess of 85 wt %.

Also provided herein is a method of preparing a monomethylcarbamyl aprophen of the formula

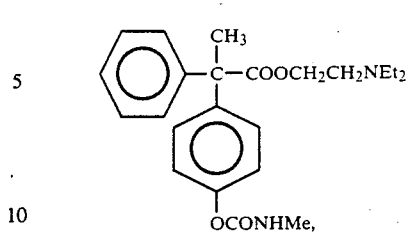 8 comprising (1) reacting p-halonitrobenzene with a alpha-methyl benzyl cyanide in a solvent to obtain a p-NO₂ phenol substituted nitrile of the formula

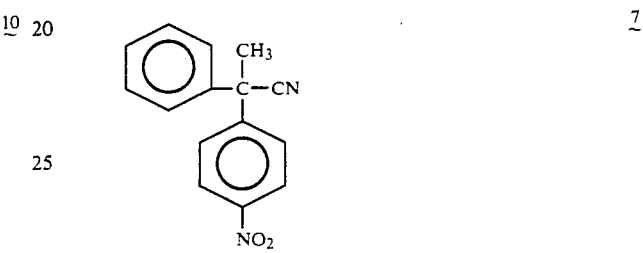 7

(2) reacting said nitrile first with sulfuric acid and then with HX, where X is Cl, Br or I to obtain the corresponding propionic acid derivative of the formula p

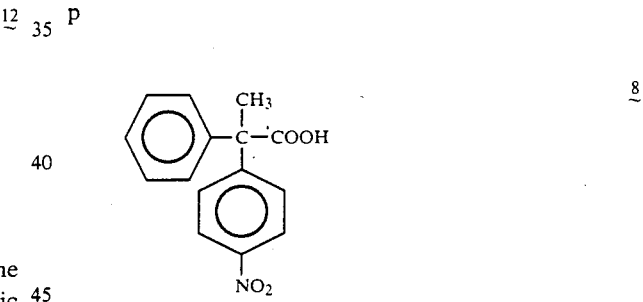 8

(3) esterifying said propionic acid derivative with a hydroxyalkyl compound to obtain an alkyl ester of the propionic acid;

(4) hydrogenating said ester to obtain an amino derivative of the propionic acid ester of the formula

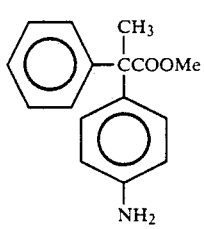 10

(5) diazotizing said amino derivative and decomposing at room temperature for at least about 72 hours to obtain a hydroxyalkyl ester of the formula

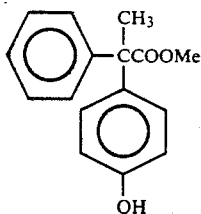

(6) hydrolyzing the hydroxyalkyl ester in an alkaline medium to obtain the corresponding hydroxy propionic acid derivative;

(7) reacting said hydroxypropionic acid derivative with an N,N-diethylaziridium salt in an aqueous solution to obtain hydroxy aprophen of the formula

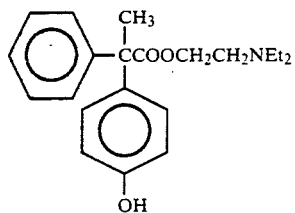

and (8) reacting said hydroxy aprophen with methylisocyanate in the presence of a catalytic amount of sodium in a solvent to obtain said monomethylcarbamyl aprophen.

Steps (1) through (7) are similar to the ones described above. In the final step, hydroxy aprophen is in this case reacted with methylisocyanate in the presence of a catalytic amount of sodium in a solvent to obtain the monomethyl carbamyl aprophen product (Compound 16).

These compounds may be further purified by known methods such as crystallization, column chromatography, solvent extraction and the like. Their structure elucidation and purity can then be determined by methods also known in the art.

Additionally, this invention provides a method of preparing a dihydroxy aprophen of the formula

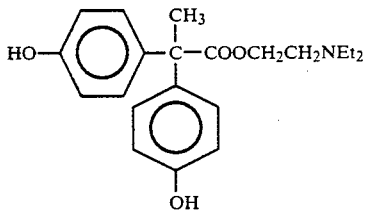

comprising (1) reacting phenol with pyruvic acid in an acidic medium to obtain 2,2-bis-(4-hydroxyphenyl) propionic acid;

(2) reacting said 2,2-bis-(4-hydroxyphenyl) propionic acid with an aqueous solution of a N,N-diethylaziridium halide in a polar solvent to obtain said dihydroxy aprophen.

The synthetic pathway of the dicarbamyl-aprophen compounds is in general outlined in Scheme I above. The key intermediate is 2,2-bis-(4-hydroxyphenyl) propionic acid (Compound 2). This compound is obtained by condensing phenyl with pyruvic acid in an acid-saturated acetic acid medium under conditions known in the art. The conversion of this acid to its diethylaminoester (Compound 3) does not proceed satisfactorily using known conventional methods such as acetyl chloride, transesterification, and the like. However, the inventors have overcome this synthetic barrier by applying their own finding that a freshly distilled N,N-dialkylaminoethyl halide can be treated for several hours at about room temperature with water to form a clear solution of the appropriate N,N-dialkylaziridinium halide in a quantitative manner. This reaction may be conducted at a temperature of about 10° to 40° C., although preferred is room temperature, for a period of about 2 to 6 hrs, preferably about 3 to 5 hrs.

Since even relatively highly concentrated solutions of the aziridinium salt are found to be stable at room temperature for weeks, these can be used as a source of aziridinium ions for the esterification reaction. Indeed, if, e.g., a sodium bicarbonate solution of compound 2 is mixed and stirred at the indicated temperature with an aqueous solution of N,N-diethylaziridinium chloride in the presence of ethyl acetate or other similar solvents the dihydroxy aprophen derivative (Compound 3) is obtained. Yields in excess of 80 wt % are typically obtained.

Also provided herein is a method of preparing a dimethylcarbamyl aprophen of the formula

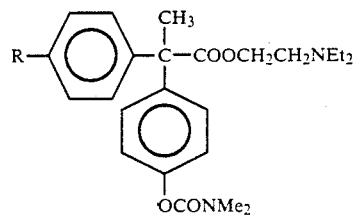

wherein R is OH or OCON(CH₃)₂, stereoisomers thereof, pharmaceutically-acceptable salts thereof or mixtures thereof, comprising (1) reacting phenol with pyruvic acid in an acidic medium to obtain 2,2-bis-(4-hydroxyphenyl) propionic acid;

(2) reacting said 2,2-bis-(4-hydroxyphenyl) propionic acid with an aqueous solution of N,N-diethylaziridium halide in a polar solvent to obtain said dihydroxy aprophen; and (3) reacting said dihydroxy aprophen with an equivalent excess of dimethylcarbamyl chloride at a temperature of about 70° to 110° C. to obtain said hydroxydimethylcarbamate aprophen (Compound 4) and bisdimethylcarbamate aprophen (Compound 5).

These products may be separated and purified by methods known in the art such as solvent extraction, recrystallization, column chromatography and the like, and then their purity determined by methods also known in the art.

Having now generally described this invention, the same will be better understood by reference to certain specific examples, which are included herein for purposes of illustration only and are not intended to be limiting of the invention or any embodiment thereof, unless so specified.

EXAMPLES

Chemistry

Melting points are determined on a Thomas-Hoover melting point apparatus and are uncorrected. $^1$H NMR spectra are obtained on a Varian XL 300 (Me$_4$Si). Mass spectra (MS) are obtained on a Finnigan 1015 mass spectrometer (chemical ionization-NH$_3$). Elemental analyses are performed by Spang Micro Analytical Laboratory (Eagle Harbor, Mich.). For purity tests, TLC is performed on fluorescent silica gel plates (Polygram Sil G/UV254), and for each of the compounds, only one spot (visualized by UV light and I$_2$ vapor) is obtained. All new compounds give satisfactory microanalyses for C, H and N within ±0.4% and/or mass spectra consistent with the assigned structures.

EXAMPLE 1

Synthesis of β-N,N-diethylaminoethyl-2,2-bis-(4-hydroxyphenyl)-propionate (3)

β-N,N-diethylaminoethylchloride (obtained from the HCl salt, and freshly distilled, 2.7 g, 0.02 mol) is suspended in 20 mL H$_2$O. After vigorous stirring for 4 hours at room temperature, the resulting clear aqueous solution which contains N,N-diethylaziridinium chloride (Leader, H., Manistersky, B., Vinche, A., unpublished results) is added in one portion to a solution of 2,2-bis-(4-hydroxyphenyl) propionic acid (Parris, C. L., Dowbenko, R., Smith, R. V., Jacobson, N. A., Pearce, J. W., Chistenson, R. M., J. Org. Chem. (1962), 27: 455) (2.6 g, 0.01 mol) in 10% NaHCO$_3$ (20 mL).

Ethyl acetate (100 mL) is added and the biphasic reaction mixture (pH 7.8) is stirred at room temperature for 48 hours. The organic phase is separated, washed with brine (2×50 mL), dried (MgSO$_4$) and evaporated to give 3.1 g (80 wt %) of a viscous oil which solidified on standing at room temperature. Purification by column chromatography (silica gel, ether saturated with NH$_3$) afforded 3 as a white solid, mp 140°–1° C.

$^1$H NMR ((CD$_3$)$_2$CO) δ–7.02 (d, 2H, J=8.7 Hz), 6.71 (d, 2H, J=8.7), 4.10 (t, 2H, J=5.9 Hz), 2.57 (t, 2H, J=5.9 Hz), 2.42 (q, 4H, J=7.0 Hz), 1.76 (s, 3H), 0.88 (t, 6H, J=7.0 Hz).

Anal. (C$_{21}$H$_{27}$NO$_4$) C,H,N.

EXAMPLE 2

Synthesis of β-N,N-diethylaminoethyl-2-(4-hydroxyphenyl)-2-(4-dimethylaminocarbamyl-oxyphenyl)propionate (4) and β-N,N-diethylaminoethyl-2,2-bis(4-dimethylaminocarbamyloxyphenyl)propionate (5)

Compound 3 (1.8 g, 0.005 mol) is dissolved in an excess of dimethylcarbamylchloride (6.0 mL). The solution is heated to 90° C. for 6 hours, cooled to room temperature and poured on ice (100 mL). After the evolution of the CO$_2$ ceases, the reaction mixture is basified with solid NaHCO$_3$ to pH 8.8 and extracted with ethyl acetate (3×100 mL). The organic phase is washed with brine (2×50 mL) and dried (MgSO$_4$), and the solvent is evaporated to give 2.0 g of a pale-brown viscous oil, which according to TLC and $^1$H NMR analysis is found to be a mixture of Compounds 4 and 5 (40:60). Separation and purification of Compounds 4 and 5 is achieved by column chromatography (silica, 5% MeOH:CHCl$_3$).

EXAMPLE 3

Characterization of Compound 4

TLC (silica, 10% MeOH:CHCl$_3$) R$_f$0.35.

$^1$H NMR (CDCl$_3$) δ7.10 (d, 2H, J=8.7 Hz), 6.95 (d, 2H, J=8.7 Hz), 6.94 (d, 2H, J=8.7 Hz), 6.56 (d, 2H, J=8.7 Hz), 4.20 (t, 2H, J=5.8 Hz), 2.98 (d, 6H, J=25.5 Hz, Me$_2$N—), 2.68 (t, 2H, J=5.8 Hz), 2.98 (d, 6H, J=25.5 Hz), 2.47 (q, 4H, J=7.1 Hz), 1.77 (s, 3H), 0.90 (t, 6H, J=7.1 Hz).

Anal. (C$_{24}$H$_{32}$N$_2$O$_5$) C,H,N.

EXAMPLE 4

Characterization of Compound 5

TLC (silica, 10% MeOH:CHCl$_3$) R$_f$0.65.

$^1$H NMR (CDCl$_3$) δ7.26 (d, 4H, J=8.7 Hz), 7.08 (d, 4H, J=8.7 Hz), 4.28 (t, 2H, J=6.0 Hz), 3.09 (d, 12H, J=24.9 Hz, Me$_2$N—), 2.73 (t, 2H, J=6.0 Hz), 2.55 (q, 4H, J=7.1 Hz), 1.93 (s, 3H), 1.02 (t, 6H, J=7.1).

Anal. (C$_{27}$H$_{37}$N$_3$O$_6$) C,H,N.

HCl salt: 175°–6° C.

EXAMPLE 5

Synthesis of 2-(4-Nitrophenyl)-2-phenylpropionitrile (Compound 7).

This compound is synthesized according to Makosza, et al with some modifications (Makosza, M., et al, Tetrahedron (1974), 30: 3723). A solution of 4-chloronitrobenzene (31.5 g, 0.2 mol) in pyridine (100 mL) is added dropwise to a vigorously stirred suspension of KOH (fine powder 70.0 g) and α-methylbenzylcyanide (26.2 g, 0.2 mol) in pyridine (150 mL), with the reaction temperature being maintained at 10° C. The reaction mixture is stirred for 24 hours at 25° C., and poured onto an excess of HCl-ice mixture. The acidic aqueous mixture is extracted with benzene, the organic phase washed with brine, dried (Na$_2$SO$_4$), and the benzene evaporated under vacuum. A crude product 42.5 g (84 wt %) results and is recrystallized from isopropanol-petroleum ether to give Compound 7 as white crystals, mp: 76°–8° C. (lit. 76° C.).

Anal. (C$_{15}$H$_{12}$N$_2$O$_2$) C,H,N.

EXAMPLE 6

Synthesis of 2-phenyl-2-(4-nitrophenyl)propionic acid (Compound 8)

The nitrile 7 (5.0 g, 0.02 mol) is dissolved in conc. H$_2$SO$_4$ and the mixture heated to 80° C. for 2 hours. The pale-brown solution is then poured onto ice and extracted with ethyl acetate (2×100 mL). The organic solvent is evaporated under reduced pressure and 48 wt % HBr solution (100 mL) is added to the remaining viscous residue. After refluxing for 8 hours, the viscous oil turns to a yellow crystalline material. The aqueous acidic phase is then removed by decantation, and the crystalline material is washed and recrystallized with H$_2$O to give 4.2 g (77 wt %) of 8.

mp: 191°–2° C. (lit. 192° C.).

$^1$H NMR (CDCl$_3$) δ8.27 (d, 2H, J=9.0 Hz), 7.55–7.40 (m, 9H), 2.1 (s, 3H).

Anal. (C$_{15}$H$_{13}$NO$_4$) C,H,N.

EXAMPLE 7

Synthesis of methyl 2-phenyl-2-(4-nitrophenyl)propionate (Compound 9)

A solution of the acid 8 (5.4 g, 0.02 mol) in a saturated solution of HCl/MeOH (150 mL) is refluxed for 16 hours. The product is isolated by conventional procedures to give 5.0 g (87 wt %) of 9 as a viscous oil. TLC (silica, 5% MeOH-CHCl$_3$) shows one spot ($R_f$ 0.65). This crude compound is used in the next step without any purification.

$^1$H NMR (CDCl$_3$) $\delta$8.06 (d, 2H, J=9.0 Hz), 7.29 (d, 2H, J=9.0 Hz), 7.25–7.15 (m, 5H), 3.68 (s, 3H), 1.89 (s, 3H).

EXAMPLE 8

Synthesis of methyl 2-phenyl-2-(4-aminophenyl)propionate (Compound 10)

A solution of 9 (2.85 g, 0.01 mol) in 95% ethanol (200 mL) is hydrogenated in the presence of 5 wt % Pd/C under 3.5 p.s.i. of hydrogen. After 24 hours, the catalyst is removed by filtration and the solution evaporated to yield 2.3 g (90 wt %) of crude viscous oil which crystallized on standing, mp 79°–80° C. (n-hexane).

$^1$H NMR (CDCl$_3$) $\delta$7.29–7.17 (m, 5H), 7.03 (d, 2H, J=8.5 Hz), 6.62 (d, 2H, J=8.5 Hz), 3.71 (s, 3H), 3.64 (brs, 2H, NH$_2$), 1.87 (s, 3H).

Anal. (C$_{16}$H$_{17}$NO$_2$) C,H,N.

EXAMPLE 9

Synthesis of methyl 2-phenyl-2-(4-hydroxyphenyl)propionate (Compound 12)

A solution of sodium nitrite (1.12 g, 0.013 mol) in 3 mL of water is added to a stirred solution of 10 (2.5 g, 0.01 mol) in 25% H$_2$SO$_4$ (15 mL) at 0° C. The mixture is stirred for 30 minutes at 0° C. and then for 72 hours at room temperature. The dark-brown oil which separates from the aqueous reaction mixture is extracted with ethyl acetate (3×100 mL) and dried over MgSO$_4$. The filtrate is evaporated and the viscous residue (2.2 g) purified by column chromatography (silica, CHCl$_3$ and 5% MeOH:CHCl$_3$). After the first fractions, which contain a considerable amount (0.6 g) of an unidentified non-polar by-product.

TLC silica-CHCl$_3$, $R_f$0.9.

$^1$H NMR (CDCl$_3$) $\delta$7.5–7.1 (m, 17H), 3.75 (s, 6H), 1.94 (s, 6H);

MS/CI: m/e 523 (M$^{+1}$)).

Compound 12 (1.4 g, 55%) is isolated as a pale-brown viscous oil.

TLC (silica, 5% MeOH:CHCl$_3$): $R_f$0.65.

$^1$H NMR (CDCl$_3$): $\delta$7.30–7.19 (m, 5H), 7.10 (d, 2H, J=8.7 Hz), 6.75 (d, 2H, J=8.7 Hz), 4.87 (s, 1H, OH), 3.73 (s, 3H), 1.89 (s, 3H).

Anal. (C$_{16}$H$_{16}$O$_3$) C,H.

Additional quantities of Compound 12 are afforded by re-extracting the original aqueous diazatization reaction mixture after allowing it to stand at room temperature for 3 to 7 days, thus increasing the total yield of Compound 12 to about 70 wt %. Attempts to facilitate the decomposition of the diazonium salt by increasing the temperature reduce the yield considerably.

EXAMPLE 10

Synthesis of 2-phenyl-2-(4-hydroxyphenyl)propionic acid (Compound 13)

A solution of Compound 12 (1.8 g, 0.007 mol) in 70 mL of 10% KOH is warmed to 80° C. for 2 hours. After cooling, the mixture is acidified with 35% HCl, and the pale-brown oil is extracted with ether (4×50 mL). After drying (MgSO$_4$), the ether is evaporated to give 1.6 g (94 wt %) of viscous oil which solidified on standing. Recrystallization from H$_2$O afforded 13 as white crystals.

mp: 136°–7° C.

$^1$H NMR (CDCl$_3$): $\delta$7.30–7.24 (m, 5H), 7.17 (d, 2H, J=8.8 Hz), 6.77 (d, 2H, J=8.8 Hz), 1.91 (s, 3H).

Anal. (C$_{15}$H$_{14}$O$_3$) C,H.

EXAMPLE 11

Synthesis of β-N,N-diethylaminoethyl-2-phenyl-2-(4-hydroxyphenyl)propionate (Compound 14)

β-N,N-diethylaminoethylchloride (freshly distilled, 2.0 g, 0.014 mol) is suspended in 15 mL H$_2$O. After vigorous stirring for 4 hours, all the oil disappears, and the clear aqueous solution obtained is added in one portion to a solution of compound 13 (1.7 g, 0.007 mol) in 30 mL of 10% NaHCO$_3$. Ethyl acetate (50 mL) is added and the biphasic reaction mixture (pH 7.8) is stirred at room temperature for 36 hours. The organic phase is separated, washed with brine (2×50 mL), dried (MgSO$_4$) and evaporated to leave 2.2 g (64 wt %) of viscous oil, which is chromatographed (silica, ether saturated with NH$_3$) to afford Compound 14 as a pale yellow viscous oil.

$^1$H NMR (CDCl$_3$) $\delta$7.31–7.18 (m, 5H), 7.10 (d, 2H, J=8.7 Hz), 4.23 (t, 2H, J=6.1 Hz), 2.68 (t, 2H, J=6.1 Hz), 2.49 (q, 4H, J=7.1 Hz), 1.89 (s, 3H), 0.96 (t, 6H, J=7.1 Hz).

Anal. (C$_{21}$H$_{27}$NO$_3$) C,H,N.

EXAMPLE 12

Synthesis of β-N,N-diethylaminoethyl-2-phenyl-2-(4-dimethylaminocarbamyloxyphenyl)propionate (Compound 15)

Compound 14 (1.05 g, 0.003 mol) is dissolved in excess dimethylcarbamylchloride (5 mL). The solution is warmed to 120° C. for 10 hours, cooled to room temperature and poured onto ice-H$_2$O (100 mL). After the evolution of the CO$_2$ ceases, the reaction mixture is basified with solid NaHCO$_3$ to pH 8.8 and extracted with ethyl acetate (3×100 mL). The combined extracts are washed with brine (2×50 mL), dried (MgSO$_4$), and the solvent evaporated. The residue is purified by column chromatography (silica, 5% MeOH/CHCl$_3$) affording 1.2 g of Compound 15 (87 wt %) as a viscous pale-yellow oil.

$^1$H NMR (CDCl$_3$) $\delta$7.28–7.21 (m, 7H), 7.04 (d, 2H, J=8.7 Hz), 4.20 (t, 2H, J=6.2 Hz), 3.05 (d, 6H, J=24.5 Hz, Me$_2$N—), 2.64 (t, 2H, J=6.2 Hz), 2.47 (q, 4H, J=7.1 Hz); 1.90 (s, 3H), 0.95 (t, 6H, J=7.1 Hz).

Anal. (C$_{24}$H$_{32}$N$_2$O$_4$) C,H,N.

EXAMPLE 13

Synthesis of
β-N,N-diethylaminoethyl-2-phenyl-2-(4-methylaminocarbamyloxyphenyl)propionate (Compound 16)

A small piece of Na (~10 mg) (Dale, F. J. and Robinson, B. J., Pharm. Pharmacol. (1970), 22: 889) is added to a solution of Compound 14 (1.5 g, 0.004 mol) and methylisocyanate (7.5 mL) in dry ether (100 mL). The reaction mixture is kept at room temperature with occasional shaking for 3 days, after which it is filtered, the filtrate evaporated and the residue purified by column chromatography (silica, 5% MeOH/CHCl$_3$) to afford 1.6 g (91 wt %) of Compound 16 as a pale yellow viscous oil.

$^1$H NMR (CDCl$_3$) δ7.30–7.21 (m, 7H), 7.05 (d, 2H, J=8.6 Hz), 5.0 (bs, 1H, NH), 4.21 (t, 2H, J=6.1 Hz), 2.89 (d, 3H, J=4.9 Hz, MeNH), 2.64 (t, 2H, J=6.1 Hz), 2.47 (q, 4H, J=7.1 Hz), 1.91 (s, 3H), 0.95 (t, 6H, J=7.1 Hz).

Anal. (C$_{23}$H$_{30}$N$_2$O$_4$) C,H,N.

EXAMPLE 14

Analysis of the Synthetic Data

Two series of carbamyl-aprophen compounds are synthesized and tested for antimuscarinic and anticholinesterase potency. In the first series, both phenyl rings of the aprophen molecule are para-substituted, while in the second, only one phenyl ring is substituted at the para-position by N-monomethylcarbamyl or N,N-dimethylcarbamyl groups.

The synthetic pathway of the disubstituted-aprophen compounds is outlined in Scheme I above. The key intermediate, 2,2-bis-(4-hydroxyphenyl) propionic acid 2, is obtained by condensing phenol with pyruvic acid in HCl-saturated acetic acid (Parris, C. L., Dowbenko, R., Smith, R. V., Jacobson, N. A., Pearce, J. W., Chistenson, R. M., J. Org. Chem. (1962), 27: 455, incorporated herein by reference in its entirety). The conversion of this acid to its diethylaminoethyl ester 3 does not proceed satisfactorily using known conventional methods (acylchloride, transesterification, etc.). In order to overcome this synthetic barrier, we utilize our recent observation (Leader, H., Manistersky, B., and Vinche, A., unpublished results) that, when freshly distilled N,N-dialkylaminoethylchlorides are treated for several hours at room temperature with water, a clear solution of the appropriate N,N-dialkylaziridinium chloride is quantitatively formed.

Since even relatively highly concentrated solutions of the aziridinium salt (~20%) are found to be stable at room temperature for weeks (based on $^1$H NMR and FAB-Mass spectrometry) (Leader, H., Manistersky, B., and Vinche, A., unpublished results), this source of aziridinium ions is used for the esterification reaction. Indeed, when a NaHCO$_3$ solution of Compound 2 is mixed and stirred at room temperature with an aqueous solution of N,N-diethylaziridinium chloride in the presence of ethyl acetate, the ester 3 is obtained in 86 wt % yield. Treatment of this compound with an excess of dimethylcarbamylchloride at 90° C. gives a mixture of the hydroxymonocarbamate 4 and the dicarbamate 5, which are separated by column chromatography.

The synthetic pathway for the mono-substituted aprophen derivatives is outlined in Scheme II above. p-chloro-nitrobenzene is reacted with α-methylbenzylcynanide 6 and the para-nitrophenyl substituted nitrile 7 is hydrolyzed via the amide to the appropriate propionic acid 8. The methyl ester 9 is hydrogenated to the amine 10 which is diazotized to Compound 11 and decomposed at room temperature to give the hydroxy methyl ester derivative 12.

Two important points should be noted with regard to the decomposition of the diazonium salt (compound 11 to 12).

First, attempts to facilitate the generation of the para-hydroxy Compound 12 by heating the acidic diazotization reaction mixture to temperatures above 40° C. fail. These attempts result in polymeric and other decomposition products. The optimal conditions for this reaction are to keep the reaction mixture at room temperature for at least about 72 hours. Secondly, a considerable amount (about 25 wt %) of an unidentified by-product is isolated by chromatography from the above reaction. According to the $^1$H NMR and MS/CI data (see, Examples), this by-product is presumably a coupling reaction product resulting from the interaction between the unreacted diazonium salt 11 and the product 12 which takes place during the relatively long period of time at room temperature.

Alkaline hydrolysis of the methyl ester 12 afforded the hydroxy acid 13 which is esterified to the hydroxy aprophen derivative 14 by interacting with N,N-diethylaziridium chloride in aqueous-bicarbonate solution. Dimethylaminocarbamyl aprophen 15 is obtained by reacting 14 with excess dimethylcarbamylchloride at about 120° C. for about 2 hours. Monomethylcarbamyl aprophen 16 is obtained by a Na-catalyzed addition reaction of methylisocyanate to 14 in ether solution. All the new compounds are purified by column chromatography, and their structural elucidation and purity are confirmed by $^1$H NMR, MS-CI and TLC.

PHARMACOLOGICAL ASSAYS

EXAMPLE 15

Determination of α-Amylase Secretion from Pancreatic Acinar Cells

Pancreatic acinar cells are prepared from male Sprague Dawley rats by three successive incubations with collagenase (0.8 mg/ml) (Gordon, R. K.; Chiang, P. K., J. Pharmacol. Exp. Ther. (1986) 236:85; Gardner, J. D. and Jensen, R. T., Am. J. Physiol. (1980) 238:G63 both of which are incorporated herein by reference in their entireties). The cells are suspended in 16 mL of Dulbecco's minimal essential medium containing 0.2% albumin, 0.01% trypsin inhibitor, and 0.09% theophylline, aerated with 100% O$_2$, and diluted 5-fold before use. Viability test results by the known trypan blue exclusion test is greater than 99%.

The acinar cells are incubated with varied doses of each compound to be tested and $10^{-5}$M carbachol in 0.5 mL. α-Amylase secreted from the acinar cells is determined with a Pharmacia Phadebas kit. I$_{50}$ values, the concentration causing a 50% decrease in α-amylase secretion, are determined using the known ALLFIT, a computer program for the analysis of inhibition curves, and converted to K$_i$ values using the K$_d$ determined from the binding of [$^{14}$C]carbachol to pancreatic acinar cells (K$_d$=3.7×$10^{-7}$M) by the method of Cheng and Prusoff (Cheng, Y.-C. and Prusoff, W. H., Biochem. Pharmacol. (1973) 22:3099 incorporated herein by reference in its entirety).

EXAMPLE 16

Determination of Acetylcholine-Induced Contraction of Guinea Pig Ileum

Distal ileum is obtained from male albino guinea pigs (350–500 g), and a segment approximately 2 cm in length is suspended in each 10 mL organ bath in oxygenated Krebs-Ringer solution maintained at 37° C. (Pankaskie, M. C. et al, J. Med. Chem (1985) 28:1117). Isometric contractions are recorded by means of a free-displacement transducer (Harvard Apparatus, Natick, Mass.) set at 1 g tension.

After a stabilization period of 45 minutes, acetylcholine (ACh) is added to the bath, allowed to act for 1 minute, and then washed out. The tissue is allowed 5 minutes to recover prior to the next addition. The maximal contractile response is designated as 100%, and other responses are reported as a percentage of that response. After a recovery period of 15 minutes, test compounds, followed 30 seconds later by ACh, are added to each bath, and the contractile responses recorded.

The $K_B$ or $pA_2$ values, measuring the affinity of an antagonist for the muscarinic receptor, are calculated using computer programs for the Schild plot (Tallarida, R. J. et al, Life Sci. (1979) 25:637).

EXAMPLE 17

Binding Assays

Freshly obtained bovine cerebral cortex is minced, mixed with an equal volume (weight/volume) of 50 mM potassium phosphate buffer, pH 7.2, containing a cocktail of protease inhibitors (0.1 mM ethylenediaminetetraacetate, 0.1 mM phenylmethylsulfonyl fluoride, and 0.02% sodium azide, and homogenized at 4° C.

The homogenate is centrifuged at 16,000×g for 1 hr at 4° C., the pellet resuspended in the same volume of buffer and centrifuged again. The pellet is resuspended in buffer and frozen in aliquots at $-30°$ C. [$^3$H]NMS ([$^3$H]N-methylscopolamine, 72 Ci/mmol, New England Nuclear, Boston, Mass.) binding to homogenized cortex is carried out in 96-well plates at 25° C. in a final volume of 0.2 mL. (Ahmad, A. et al, FEBS Lett. (1987) 214:285).

The concentration of [$^3$H]NMS was 2 nM, and non-specific binding is determined in the presence of 1 μM atropine. $K_i$ values are determined as for the α-amylase assay by using the $K_d$ calculated for [$^3$H]NMS binding to cortex by Scatchard analysis ($K_d = 3.2 \times 10^{-10}$M).

EXAMPLE 18

Study of Cholinesterase Assay and Inhibition Kinetics

The activities of human serum butyrylcholinesterase, electric eel acetylcholinesterase (EC 3.1.1.8 and EC 2.1.1.7, respectively, Sigma Chem. Co., St. Louis, Mo.), and fetal bovine serum acetylcholinesterase (Ralston, J. S. et al, J. Biol. Chem. (1985) 260:4312) are determined calorimetrically by the method of Ellman, (Ellman, G. L. et al, Biochem. Pharmacol. (1961) 7:88) as described by Main et al, E. Biochem. J. (1974) 143:733). The reactions are carried out at 30° C. in 0.1M sodium phosphate buffer at pH 8.0 in the presence of $10^{-3}$M butyrylthiocholine or acetylthiocholine and $3.3 \times 10^{-4}$M 3-carboxy-4-nitrophenyl disulfide. Aliquots of incubating mixtures containing enzyme alone, or enzyme in the presence of each carbamate, are withdrawn at selected time intervals and assayed for enzyme activity in order to obtain kinetic data. From the kinetic data, inhibition and bimolecular rate constants are calculated by the following equation $$\frac{1}{k_{app}} = \frac{1}{k_3} + \frac{K_I}{k_3} \times \frac{1}{[I]}$$

in which $k_{app}$ is the pseudo-first order rate constant. The bimolecular rate constant ($k_3'$) is equal to $k_3/K_I$ (Main et al, E. Biochem. J. (1974) 143:733); Main et al, Science (1966) 154:400).

EXAMPLE 19

Measurements of Antimuscarinic Activities

The results of these studies are shown in Table I herebelow.

TABLE I

ANTIMUSCARINIC ACTIVITY OF CARBAPHEN ANALOGS AND STANDARD COMPOUNDS*

| | Inhibition of | | | |
|---|---|---|---|---|
| | Guinea Pig Ileum Contraction | | Pancreatic Acini α-amylase Release | Cerebral cortex [$^3$H]NMS binding |
| Compound | $pA_2$ | [$K_B$ (M)] | $K_i$ (M) | $K_i$ (M) |
| Monomethyl carbaphen (16) | 7.3 ± 0.1 | $5.0 \times 10^{-8}$ | $2.0 \pm 0.9 \times 10^{-9}$ | $2.6 \pm 1.5 \times 10^{-8}$ |
| Dimethyl carbaphen (15) | 7.1 ± 0.1 | $8.3 \times 10^{-8}$ | $4.2 \pm 0.9 \times 10^{-8}$ | $1.5 \pm 0.5 \times 10^{-7}$ |
| Hydroxy aprophen (14) | 7.2 ± 0.3 | $7.0 \times 10^{-8}$ | $5.6 \pm 1.2 \times 10^{-9}$ | $1.0 \pm 0.5 \times 10^{-7}$ |
| Dihydroxy aprophen (3) | 5.7 ± 0.1 | $2.0 \times 10^{-6}$ | $4.9 \pm 0.8 \times 10^{-6}$ | $2.1 \pm 0.2 \times 10^{-6}$ |
| Dimethylhydroxy carbaphen (4) | 5.5 ± 0.2 | $3.2 \times 10^{-6}$ | $2.4 \pm 0.8 \times 10^{-6}$ | $3.4 \pm 0.3 \times 10^{-6}$ |
| Bisdimethyl carbaphen (5) | not active | | not active | marginal activity |
| Aprophen | 8.5 ± 0.1 | $3.1 \times 10^{-9}$ | $1.7 \pm 0.7 \times 10^{-9}$ | $5.1 \pm 1.0 \times 10^{-8}$ |
| Atropine | 8.7 ± 0.1 | $2.0 \times 10^{-9}$ | $1.6 \pm 1.1 \times 10^{-9}$ | $2.4 \pm 0.7 \times 10^{-9}$ |
| Pirenzepine | 4.3 ± 0.4 | $5.0 \times 10^{-5}$ | $1.2 \pm 0.2 \times 10^{-7}$ | $1.7 \pm 0.7 \times 10^{-7}$ |

*Each inhibition constant represents the mean of four to five independent experiments ± standard errors of the mean.

Table I shows that the most potent antimuscarinic analog is obtained by substituting a monomethylcarbamate moiety at the para-position of one phenyl ring of aprophen, monomethyl carbaphen (16). The $pA_2$ for monomethyl carbaphen is 7.3±0.1 ($K_B = 5.0 \times 10^{-8}$M) when tested on the acetylcholine-induced contraction of guinea pig ileum, which has predominantly the $M_2$ receptor subtype. (Witkin et al, J. Pharmacol. Exp. Ther. (1987) 242:796; Carroll et al, J. Med. Chem. (1987) 30:805; Watson et al, Life Sci. (1983) 32:3001; Hammer, R. et al Life Sci. (1982) 31:2991, Birdsall et al, Trends Pharmacol. Sci. (1984) 5, Supp. 4; Smejkal, R. M. et al, Gen. Pharmacol., in press).

It inhibits the carbachol-induced release of α-amylase from pancreatic acinar cells, which have an $M_2$ receptor subtype that may be different from that of ileum, with a $K_i$ of $2.0\pm0.9\times10^{-9}$M. (Otsuki, M., et al, Gastroenterology (1985) 89:408; Korc, M. et al, J. Pharmacol. Exp. Ther. (1987) 240:118).

With respect to the inhibition of [$^3$H]NMS binding to cerebral cortex membranes, which contain predominantly the $M_1$ receptor subtype, (Watson, M., et al, Life Sci. (1983) 32:3001; Birdsall, N. J. M., et al, Trends Pharmacol. Sci. (1984) 5, Supp. 4; Hammer, R., et al, Life Sci. (1982) 31:2991; Watson, M. et al, Life Sci. (1982) 31:2019; McKinney, M. et al; Ann. Rev. Pharmacol. Toxicol. (1985) 24:121; McKinney, M. et al, Mol. Pharmacol. (1985) 27:223), the $K_i$ is $2.6\pm1.5\times10^{-8}$M. Overall, the antimuscarinic profile of monomethyl carbaphen is very similar to that of aprophen (Table I), with the former showing more specificity for the pancreatic $M_2$ receptor subtype over the $M_1$ subtype of the cortex.

While the $pA_2$ value for the inhibition of ileum contraction by dimethyl carbaphen (Compound 15) is about the same as that of monomethyl carbahen (Compound 16), the inhibition of $\alpha$-amylase release and [$^3$H]NMS binding are each one order of magnitude lower (Table I). Substitution with a para-dimethylcarbamate on one phenyl ring of aprophen and a para-hydroxyl group on the other (dimethyl-hydroxy carbaphen (4)) is not well tolerated. The antimuscarinic activities of Compound 4 are one to two orders of magnitude lower than those of dimethyl carbaphen. Bisdimethyl carbaphen (5), a compound with para-dimethylcarbamate substitution on both phenyl rings of aprophen, is inactive. In comparing the inhibition constants of Compounds 15, 4, and 5, it is evident that these carbaphen analogs do not exhibit any muscarinic subtype specificity.

Interestingly, the mono-para-hydroxy-substituted aprophen (hydroxy aprophen, Compound 14), which is both the synthetic precursor of mono and dimethyl carbaphen and the decarbamylated end product, is almost as potent an antimuscarinic as monomethyl carbaphen and shows the most preference for the $M_2$ subtype of the pancreas over the $M_1$ subtype of the cerebral cortex (about 18-fold). However, the addition of a second para-hydroxyl group to aprophen (dihydroxy aprophen (Compound 3)) leads to a drastic decrease in the antimuscarinic activities with inhibition constants in the region of $10^{-6}$M.

These structure-activity relationship data suggest that one of the phenyl rings of aprophen must remain unsubstituted in order to preserve antimuscarinic activity, while the substitution of a carbamate or hydroxyl function in the para-position of the other phenyl ring is well tolerated. This is evident from the poor antimuscarinic potency of dihydroxy aprophen (Compound 3) and dimethyhydroxy carbaphen (Compound 4), and the lack of activity of bisdimethyl carbaphen (Compound 5) and contrasts with the potent antimuscarinic activity of Compounds 14, 15, and 16 which have one unsubstituted phenyl ring.

EXAMPLE 20

Measurement of Anticholinesterase Activity

When tested for their ability to inactivate human serum butyrylcholinesterase, i.e., carbamylating ability, the four carbaphen analogs, monomethyl carbaphen (Compound 16), dimethyl carbaphen (Compound 15), dimethylhydroxy carbaphen (Compound 4) and bisdimethyl carbaphen (Compound 5) show a potent ability to carbamylate butyrylcholinesterase. These data are shown in Table II herebelow.

TABLE II

ANTI-BUTYRLCHOLINESTERASE (HUMAN) ACTIVITY OF CARBAPHEN ANALOGS* AND STANDARD COMPOUNDS

| Carbamates | $K_I$ (M) | bimolecular rate constant, $k_3'$ (liter/mole min) |
|---|---|---|
| Monomethyl carbaphen (16) | $1.4 \pm 0.6 \times 10^{-6}$ | $8.5 \pm 4.2 \times 10^5$ |
| Dimethyl carbaphen (15) | $1.3 \pm 1.0 \times 10^{-6}$ | $6.6 \pm 3.5 \times 10^5$ |
| Dimethylhydroxy carbaphen (4) | $0.8 \pm 0.5 \times 10^{-6}$ | $3.0 \pm 2.3 \times 10^5$ |
| Bisdimethyl carbaphen (5) | $4.6 \pm 0.3 \times 10^{-6}$ | $1.4 \pm 0.8 \times 10^4$ |
| Pyridostigmine | $3.5 \pm 1.3 \times 10^{-6}$ | $3.4 \pm 1.1 \times 10^4$ |
| Physostigmine | $5.0 \pm 2.4 \times 10^{-6}$ | $7.0 \pm 0.9 \times 10^4$ |

*Each inhibition constant represents the mean of four to five independent experiments ± standard errors of the mean.

It should be noted that aprophen, itself, is not subject to hydrolysis by human serum butyrylcholinesterase. (Aarbakke, J. et al, J. Pharm. Pharmacol. (1986) 38:928. The $K_I$ values are on the order of $10^{-6}$M, similar to those of pyridostigmine and physostigmine, which are clinically useful carbamates.

In contrast to the inhibition of butyrylcholinesterase, the carbaphen analogs do not inhibit in a time-dependent manner the activity of acetylcholinesterase purified from fetal bovine serum or obtained from electric eel at concentrations of carbaphens from about $10^{-7}$ to $10^{-5}$M. However, at about $10^{-4}$M, all four carbaphen analogs, monomethyl carbaphen (Compound 16), dimethyl carbaphen (Compound 15), dimethyl hydroxy carbaphen (Compound 4) and bisdimethyl carbaphen (Compound 5), did inhibit in a time-dependent manner the activity of fetal bovine serum acetylcholinesterase by about 17 to 40%.

These results are consistent with the inhibition, observed using steady-state kinetics, produced by aprophen and other aromatic/neurotoxic agents, which preferentially inhibit butyrylcholinesterase over acetylcholinesterase. Similar results with additional compounds lead to the conclusion that butyrylcholinesterase, in comparison with acetylcholinesterase, contains a unique hydrophobic site which partially determines the substrate and inhibitor patterns of butyrylcholinesterase. (Kabachnik, M. I. et al, Pharmacol. Revs. (1970) 22:355; Augustinsson, K., B. Biochim. Biophys. Acta (1966) 128:351).

IN VIVO STUDIES

EXAMPLE 21

Animal Studies with a Monomethyl Carbaphen (Compound 16) Pretreatment

A highly toxic anti-cholinesterase organophosphate, 7-(methylethoxyphosphinyloxy)-1-methylquinolinium iodide (MEPQ) is used for these in vivo studies. This compound inhibits acetylcholinesterase at an extremely high rate with a 1:1 stoichiometry (Levy, D. and Ashani, Y. Biochem. Pharm. 35, 1079–1085, 1986).

The $LD_{50}$ in guinea pigs is found to be approximately 25 ug/kg. This permits the use of very small volumes of the MEPQ compound.

Guinea pigs which receive no pretreatment die within
 (1) about 15 min after i.m. exposure to 2 $LD_{50}$ of MEPQ; and (2) within 10 min after i.m. exposure to 4 LD$_{50}$ of MEPQ.

Following a 30 min pretreatment dose of monomethyl carbaphen (Compound 16) sufficient to inhibit cholinesterase in vivo by about 60%, guinea pigs can survive a challenge of 2 LD$_{50}$ of MEPQ.

Of five pretreated animals challenged with 4 LD$_{50}$ of MEPQ,
(1) two animals died after about 15 min,
(2) one died after about 45 min, and
(3) two survived the crisis and were still alive and feebly moving around at the end of the day.

Thus, monomethyl carbaphen evidences protective characteristics against multiple LD$_{50}$ doses of a potent organophosphate, even in the absence of treatment with other supportive drugs subsequent to the above.

The magnitude of the inhibition constants of the carbaphen analogs show that, in contrast to the stearic requirements of the muscarinic receptors, bulky phenyl ring substitutions of aprophen can be tolerated by butyrycholinesterase. The reason the analogs are not as active against acetylcholinesterase is unclear. However, it is important to note that both 15 and 16, after carbamylating butyrylcholinesterase, produce as an end product hydroxy aprophen (Compound 14), itself a potent antimuscarinic (Table I). Thus, the carbaphen analogs, monomethyl carbaphen (Compound 16) and dimethyl carbaphen (Compound 15), are binary prototype drugs that are potent both as antimuscarinic agents and as carbamates. Therefore, these compounds show promise as prophylactic/thera-peutic antidotes for organophosphate poisoning, as well as being candidates for combination treatment modalities.

The invention now being fully described, it will be apparent to one of ordinary skill in the art that many changes and modifications can be made thereto without departing from the spirit or scope of the invention as set forth herein.

We claim:

1. An organophosphate poisoning inhibitory composition, comprising an organophosphate poisoning inhibitory amount of a compound of the formula

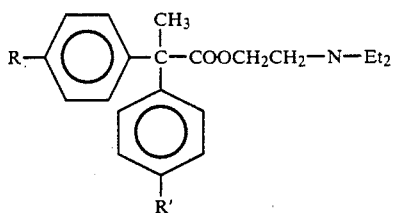

wherein
R is OH or OCON(CH$_3$)$_2$; and
R' is H, OH or OCON(CH$_3$)$_2$, provided that when R is OH, R' cannot be H; stereoisomers thereof, pharmaceutically-acceptable salts thereof or mixtures thereof.

2. The composition of claim 1, comprising about 0.010 to 99.990 wt % of the compound.

3. A method of inhibiting organophosphate poisoning, comprising
administering to a subject in need of said inhibition an amount of the compound of claim 1 effective to attain said inhibition.

4. The method of claim 3, wherein the compound is prophylactically administered prior to organophosphate poisoning.

5. A method of treating a subject afflicted with organophosphate poisoning comprising administering to said subject an amount of the compound of claim 1 effective to ameliorate said condition.

6. A method of treating a subject afflicted with coronary insufficiency comprising administering to said subject an anti-coronary insufficiency effective amount of the compound of claim 1.

7. A method of treating a subject afflicted with cerebral vasospasms comprising administering to said subject an anti-cerebral vasospasmic effective amount of the compound of claim 1.

8. A method of treating a subject afflicted with spasmic cholitis comprising administering to said subject an anti-cholitis effective amount of the compound of claim 1.

9. A method of treating a subject afflicted with cholecystitis comprising administering to said subject an anti-cholicystitis effective amount of the compound of claim 1.

10. A method of preparing a hydroxy aprophen of the formula

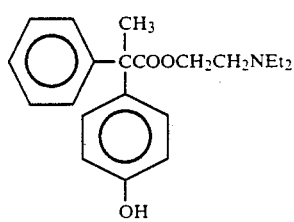

stereoisomers thereof, pharmaceutically-acceptable salts thereof or mixtures thereof, comprising
(1) reacting p-halonitrobenzene with alpha-methylbenzyl cyanide in a solvent to obtain a p-NO$_2$ phenol substituted nitrile of the formula

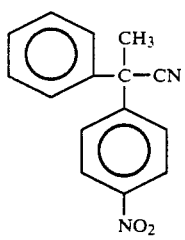

(2) reacting said nitrile first with sulfuric acid and then with HX, where X is Cl, Br or I to obtain the corresponding propionic acid derivative of the formula p

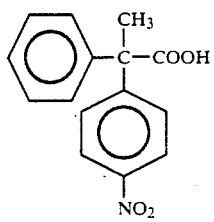

(3) esterifying said propionic acid derivative with an hydroxyalkyl compound to obtain an alkyl ester of the propionic acid;

(4) hydrogenating said ester to obtain an amino derivative of the propionic acid ester of the formula

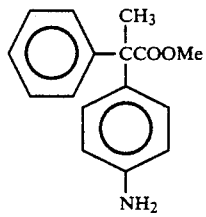

10

(5) diazotizing said amino derivative and decomposing at room temperature for at least about 72 hours to obtain a hydroxyalkyl ester of the formula

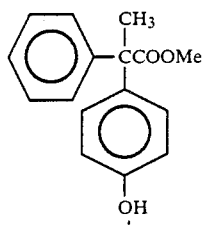

12

(6) hydrolyzing the hydroxyalkyl ester in alkaline medium to obtain the corresponding hydroxy propionic acid derivative;

(7) reacting said hydroxy propionic acid derivative with an N,N-diethylaziridium salt in an aqueous solution to obtain said hydroxy aprophen of the formula

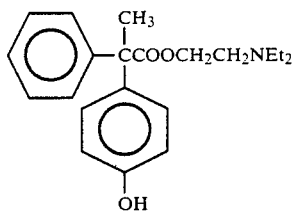

14 stereoisomers thereof, pharmaceutically-acceptable salts thereof and mixtures thereof.

11. A method of preparing a dimethylaminocarbamyl aprophen of the formula

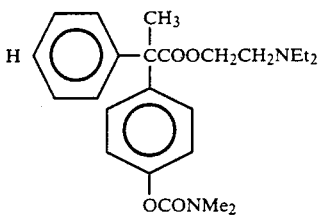

stereoisomers thereof, pharmaceutically-acceptable salts thereof or mixtures thereof comprising (1) reacting p-halonitrobenzene with alpha-methylbenzyl cyanide in a solvent to obtain a p-NO₂ phenol substituted nitrile of the formula

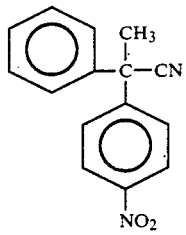

7

(2) reacting said nitrile first with sulfuric acid and then with HX, where X is Cl, Br or I to obtain the corresponding propionic acid derivative of the formula p

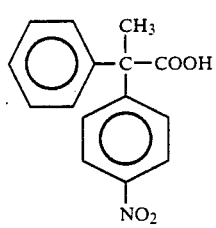

8

(3) esterifying said propionic acid derivative with an hydroxyalkyl compound to obtain an alkyl ester of the propionic acid;

(4) hydrogenating said ester to obtain an amino derivative of the propionic acid ester of the formula

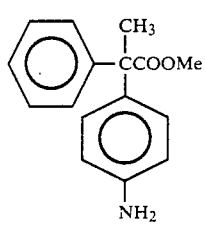

10

(5) diazotizing said amino derivative and decomposing at room temperature for at least about 72 hours to obtain a hydroxyalkyl ester of the formula

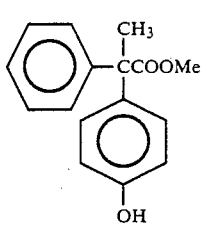

12

(6) hydrolyzing the hydroxyalkyl ester in an alkaline medium to obtain the corresponding hydroxy propionic acid derivative;

(7) reacting said hydroxy propionic acid derivative with an N,N-diethylaziridium salt in an aqueous solution to obtain hydroxy aprophen of the formula

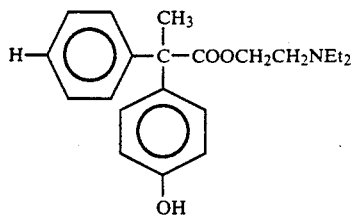

and (8) reacting said hydroxy aprophen with an equivalent excess of dimethylcarbamyl halide at a temperature of about 80° to 140° C. to obtain said dimethylaminocarbamyl aprophen.

12. A method of preparing a dihydroxy aprophen of the formula

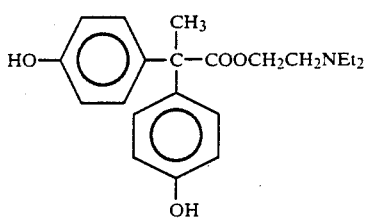

steroisomers' thereof, pharmaceutically-acceptable salts thereof or mixtures thereof, comprising (1) reacting phenol with pyruvic acid in an acidic medium to obtain 2,2-bis-(4-hydroxyphenyl) propionic acid; and (2) reacting said 2,2-bis-(4-hydroxyphenyl) propionic acid with an aqueous solution of a N,N-diethylaziridium halide in a polar solvent to obtain said dihydroxy aprophen.

13. A method of preparing a dimethyl carbamate aprophen of the formula

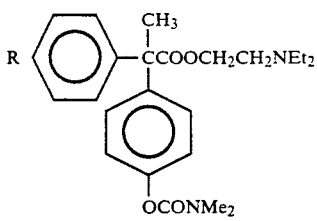

wherein R is OH or OCON(CH$_3$)$_2$, stereoisomers thereof, pharmaceutically-acceptable salts thereof or mixtures thereof, comprising (1) reacting phenol with pyruvic acid in an acidic medium to obtain 2,2-bis-(4-hydroxyphenyl) propionic acid;

(2) reacting said 2,2-bis-(4-hydroxyphenyl) propionic acid with an aqueous solution of a N,N-diethylaziridium halide in a polar solvent to obtain said dihydroxy aprophen; and (3) reacting said dihydroxy aprophen with an equivalent excess of dimethylcarbamyl chloride at a temperature of about 70° to 110° C. to obtain said hydroxydimethylcarbamate aprophen or bisdimethyl carbamate aprophen.

14. A method of preparing a monomethylcarbamyl aprophen of the formula

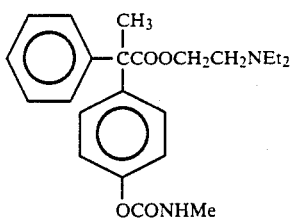

stereoisomers thereof, pharmaceutically-acceptable salts thereof or mixtures thereof, comprising (1) reacting p-halonitro benzene with alpha-alkylbenzyl cyanide in a solvent to obtain a p-NO$_2$ phenol substituted nitrile of the formula

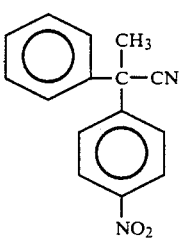

(2) reacting said nitrile first with sulfuric acid and then with HX, where X is Cl, Br or I to obtain the corresponding propionic acid derivative of the formula p

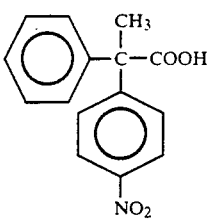

(3) esterifying said propionic acid derivative with a hydroxyalkyl compound to obtain an alkyl ester of the propionic acid;

(4) hydrogenating said ester to obtain an amino derivative of the propionic acid ester of the formula

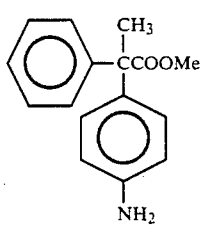

(5) diazotizing said amino derivative and decomposing at room temperature for at least about 72 hours to obtain a hydroxyalkyl ester of the formula

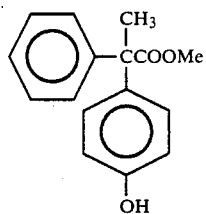

12

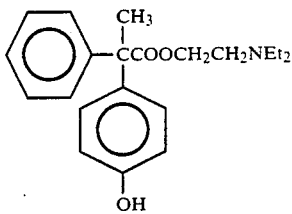

14

(6) hydrolyzing the hydroxyalkyl ester in an alkaline medium to obtain the corresponding hydroxy propionic acid derivative;

(7) reacting said hydroxy propionic acid derivative with an N,N-diethylaziridium salt in an aqueous solution to obtain hydroxy aprophen of the formula stereoisomers thereof, pharmaceutically-acceptable salts thereof or mixtures thereof; and (8) reacting said hydroxy aprophen with methylisocyanate in the presence of a catalytic amount of sodium in a solvent to obtain said monomethylcarbamyl aprophen.

* * * * *